United States Patent [19]

Buckley

[11] Patent Number: 4,577,037

[45] Date of Patent: Mar. 18, 1986

[54] METHODS FOR PREVENTING THE PRECIPITATION OF MIXED ZINC DIALKYLDITHIOPHOSPHATES WHICH CONTAIN HIGH PERCENTAGES OF A LOWER ALKYL GROUP

[75] Inventor: Thomas F. Buckley, Hercules, Calif.

[73] Assignee: Chevron Research, San Francisco, Calif.

[21] Appl. No.: 579,067

[22] Filed: Feb. 10, 1984

[51] Int. Cl.$^4$ .............................................. C07F 3/06
[52] U.S. Cl. ...................................................... 556/25
[58] Field of Search ......................... 260/429.9; 556/25

[56] References Cited

U.S. PATENT DOCUMENTS

| | | | |
|---|---|---|---|
| 2,680,123 | 6/1954 | Mulvany | 260/429.9 |
| 3,000,822 | 9/1961 | Higgins et al. | 260/429.9 X |
| 3,234,250 | 2/1966 | Schneider et al. | 260/429.9 |
| 3,290,347 | 12/1966 | Miller | 260/429.9 |
| 3,293,181 | 12/1966 | Stuart | 260/429.9 X |
| 3,347,790 | 10/1967 | Meinhardt | 260/429.9 X |
| 3,562,306 | 2/1971 | Blaha et al. | 260/429.9 |
| 3,826,745 | 7/1974 | Ryer et al. | 252/32.7 E |
| 4,085,053 | 4/1978 | Caspari | 252/32.7 |
| 4,215,067 | 7/1980 | Brannen et al. | 260/429.9 |
| 4,377,527 | 3/1983 | Sabol et al. | 260/429.9 |
| 4,496,495 | 1/1985 | Casperi et al. | 260/989 |

FOREIGN PATENT DOCUMENTS 2104898A  3/1983  United Kingdom.

*Primary Examiner*—Helen M. S. Sneed
*Attorney, Agent, or Firm*—S. R. LaPaglia; R. CC. Gaffney; G. F. Swiss

[57] ABSTRACT

Precipitation of a mixed zinc dialkyldithiophosphate prepared from a mixture of about 50-80 mole percent of a lower alcohol plus 50-20 mole percent of a higher alcohol may be prevented by the addition to the reaction system used to prepare the mixed zinc composition of from about 0.5 to 2.0 percent by weight of an ammonium salt of an acid.

5 Claims, No Drawings

METHODS FOR PREVENTING THE PRECIPITATION OF MIXED ZINC DIALKYLDITHIOPHOSPHATES WHICH CONTAIN HIGH PERCENTAGES OF A LOWER ALKYL GROUP

BACKGROUND OF THE INVENTION

1. Field of the Invention

This invention pertains to a method of preparing mixed zinc dialkyldithiophosphate compositions which are not prone to precipitation under normal storage conditions. In particular, this invention is directed to the addition of an ammonium salt of an acid during the preparation of the zinc compositions of this invention. The ammonium salt substantially retards the susceptibility of the mixed zinc dialkyldithiophosphate compositions to form a precipitate, thus improving its solution stability.

2. Description of the Prior Art

Zinc salts of dialkyldithiophosphoric acids are known to inhibit the oxidation of the lubricant oil while improving the anti-corrosion property of the lubricant oil composition. It is also known that the alkyl groups of these zinc dialkyldithiophosphates may be of high molecular weight or low molecular weight. Zinc dialkyldithiophosphates wherein the alkyl groups are of four carbon atoms or less are considerably less expensive than the zinc dialkyldithiophosphates containing alkyl groups derived from alcohols having five or more carbon atoms. In spite of this, these zinc dialkyldithiophosphates containing only alkyl groups derived from alcohols having four or fewer carbon atoms have not been widely marketed as lubricating oil additives. Reasons for this have been that these zinc di(loweralkyl)dithiophosphates are insufficiently oil soluble to allow preparation of a concentrate. Moreover, the normally liquid compositions of the low molecular weight zinc dialkyldithiophosphates are prone to precipitation (crystallization).

Normally, the zinc dialkyldithiophosphate additives of this invention should be oils and are transported either neat, that is only as the zinc dialkyldithiophosphate, or as a lubricating oil concentrate. In any event, precipitation of a portion of the additive during transport requires that the precipitate be solubilized prior to formulation.

In order to overcome this problem, U.S. Pat. Nos. 2,680,123; 3,151,075; 3,000,822; 3,385,791 and others teach the use of zinc dialkyldithiophosphates prepared from a mixture of a low molecular weight alcohol and a high molecular alcohol. This results in mixture of products containing a statistical distribution of pure zinc di(loweralkyl)dithiophosphate, zinc mixed-dialkyldithiophosphates and pure zinc di(higheralkyl)dithiophosphate as shown in the formula below:

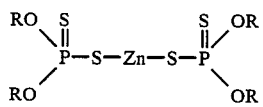

I wherein R may be either a lower or higher alkyl group.

The use of the mixed alcohols improves the oil solubility of the resulting product while also lowering its overall costs.

However, as the mole percent of the lower alcohol to the total alcohol employed in preparing the mixed dialkyldithiophosphate exceeds approximately 50 percent, problems with the solution stability of the resulting zinc dialkyldithiophosphate composition are raised again. This problem results in a precipitate forming in the zinc dialkyldithiophosphate solutions. This problem of precipitation in mixed zinc dialkyldithiophosphates of high lower alkyl content is most apparent when the lower alkyl methyl, ethyl, n-propyl; and isopropyl groups are employed but also arises when isomers of butyl alcohol are employed. This is particularly evident when the amount of butyl alcohol used to form the mixed zinc dialkyldithiophosphate is raised to approximately 75-80 mole percent of the total alcohol content.

Without being limited to any particular theory, it is believed that, as the level of the lower alcohol employed to form the mixed zinc dialkyldithiophosphate is raised, the statistical distribution of products favors greater amounts of pure zinc di(loweralkyl)dithiophosphate (wherein all the R groups in FIG. 1 are the same lower alkyl group). These pure zinc di(loweralkyl)dithiophosphates are known to be prone to crystallization in solution and to be both insoluble in oil. Thus, although the use of a lower alcohol is economically favorable, the use of increasing the amounts of the lower alcohol results in solubility and crystallinity problems in the product.

Accordingly, the use of a mixture of lower and higher alcohols in preparing mixed zinc dialkyldithiophosphates is limited to mole ratios of lower to higher alcohols which favor a low statistical proportion of pure zinc di(loweralkyl)dithiophosphate. Nevertheless, the use of a maximum amount of the lower alcohol is economically advantageous and thus a solution which alleviates the problems of precipitation and solubility associated with the use of large amounts of the lower alcohol would be particularly beneficial.

This invention is directed to a method of preparing mixed zinc dialkyldithiophosphate compositions which are not prone to precipitation under normal storage conditions.

I have now found that precipitation (crystallization) on mixed zinc dialkyldithiophosphate compositions prepared from the reaction of phosphorus pentasulfide with a mixture of about 50-80 mole percent of a lower alcohol plus 50-20 mole percent of a higher alcohol followed by neutralization of the resulting dialkyldithiophosphoric acid with a basically reacting zinc compound may be alleviated by the addition to the reaction mixture of an effective amount of an ammonium salt to prevent precipitation of the resulting mixed zinc dialkyldithiophosphate. The use of an ammonium salt is also effective in preventing the precipitation of a mixed zinc dialkyldithiophosphate in an oil concentrate.

U.S. Pat. No. 4,085,053 discloses that metal dithiophosphates may be prepared by the neutralization of dithiophosphoric acid with a metal base in the presence of an acidic promoter followed by reacting a substantial portion of excess acidic promoter with a weak base. Among others this reference discloses acetic acid as an example of a promoter in the preparation of the metal dialkyldithiophosphates and ammonia (ammonium hydroxide) as an example of a weak base.

The addition of alkylamines or arylamines to a lubricating oil composition containing a zinc dithiophosphate is taught by U.S. Pat. Nos. 2,766,207; 3,284,354; and 3,018,247 among others.

U.S. Pat. No. 3,826,745 discloses amine salts of mixed acid phosphates as useful in inhibiting haze or precipitation formation in zinc dialkyldithiophosphates caused by small amounts of water.

U.S. Pat. No. 4,377,527 and Belgium Application No. 894,196 disclose the use of an ammonia-producing compound (such as ammonium salts of mineral acids and organic acids) as a catalyst in the neutralization reaction between a dihydrocarbyl dithiophosphoric acid and a basically reacting zinc compound. This reference further teaches that suitable ammonium producing species are those which will decompose to ammonia or ammonium and includes, for example, ammonium acetate.

SUMMARY OF THE INVENTION

The present invention relates to a process for the preparation of a mixed zinc dialkyldithiophosphate by the reaction of phosphorus pentasulfide with a mixture of a lower alcohol and a higher alcohol followed by neutralization of the resulting mixed dialkyldithiophosphoric acid with a basically reacting zinc compound, wherein the improvement comprises the addition to said reaction of an effective amount of an ammonium salt of an acid to prevent precipitation of said mixed zinc composition.

Preferably, about 0.5 to 2.0 percent by weight of the ammonium salt of an acid is added to the reaction. The range 0.5 to 2.0 percent by weight is based upon the amount of zinc dialkyldithiophosphate which would theoretically be formed in the reaction.

Preferably, the mixed zinc dialkyldithiophosphates are prepared by reacting phosphorus pentasulfide with a mixture of about 50-80 mole percent of a lower alcohol plus 50-20 mole percent of a higher alcohol followed by neutralization of the resulting dialkyldithiophosphoric acid with a basically reacting zinc compound such as zinc oxide.

A particularly preferred lower alcohol used in preparing the mixed zinc dialkyldithiophosphates is isopropanol. A particularly preferred higher alcohol is 2-ethylhexanol.

In a preferred aspect of the present invention, the mixed zinc dialkyldithiophosphate is prepared from a mixture of 70 mole percent of isopropanol/30 mole percent of 2-ethylhexanol.

When the lower alcohol employed in preparing the mixed zinc dialkyldithiophosphate is either isopropanol or a butanol isomer as much as 85 mole percent of the lower alcohol may be employed in the alcoholic mixture with the resulting mixed zinc solution still effectively stabilized by the addition of the ammonium salt.

Preferred ammonium salts of acids are the ammonium salts of carboxylic acids containing from 1 to 6 carbon atoms. Most preferably, the ammonium sat employed in the instant invention is ammonium acetate.

As employed herein, the following terms have the following meaning unless expressly stated to the contrary.

The term "mixed zinc dialkyldithiophosphate" means zinc dialkyldithiophosphates prepared from the reaction of phosphorus pentasulfide (or its equivalent) with a mixture of a lower alcohol and a higher alcohol followed by neutralization of the resulting dialkyldithiophosphoric acid with a basically reacting zinc compound.

The term "prevent(ing) the precipitation of mixed zinc dialkyldithiophosphates" does not mean that precipitation will be prevented under all conditions but refers to the retardation of precipitation at normal storage conditions of about 0°–50° C. for a period of up to 6 months.

The term "lower alcohol" means alcohols having four or fewer carbon atoms and includes for instance ethanol, n-propanol, isopropanol, n-butanol, isobutanol, sec-butanol and t-butanol.

The term "higher alcohol" means alcohol having 5–18 carbon atoms and includes for instance n-pentanol, n-hexanol, 2-ethylhexanol, n-decanol and the like.

The term "ammonium salt of an acid" refers to ammonium salts of inorganic acids plus the ammonium salts of carboxylic acids having 1 to 6 carbon atoms.

Ammonium salts of inorganic acids include, for instance, ammonium bromide, ammonium carbonate, ammonium chloride, ammonium chromate, ammonium fluoride, ammonium iodide, ammonium molybdate, ammonium nitrate, ammonium sulfate, ammonium zinc sulfate and the like.

Ammonium salts of carboxylic acids having from 1 to 6 carbon atoms include, for instance, ammonium acetate, ammonium propionate, ammonium butyrate, ammonium citrate, ammonium oxalate and the like.

It will be understood that in the context of this invention other salts of zinc dialkyldithiophosphate may be considered as substitutes for zinc. Examples of such salts are the nickel salts, barium salts, copper salts, magnesium salts, sodium salts, calcium salts and the like.

Likewise, other phosphorus sulfides may be employed as substitutes for phosphorus pentasulfide and are considered as equivalent of phosphorus pentasulfide, such phosphorus sulfides includes $P_5S_7$, $P_4S_8$ etc. However, for reasons of low cost reactivity and availability, phosphorus pentasulfide ($P_2S_5$) is preferred.

DETAILED DESCRIPTION OF THE INVENTION

The compositions of this invention may be conveniently prepared by adding the desired amount of an ammonium salt during the preparation of the mixed zinc dialkyldithiophosphate.

The ammonium salts employed in this invention are commercially available.

The ammonium salt may be added at any stage of the reaction. Preferably, the ammonium salt is added with the dialkyldithiophosphoric acid during the neutralization reaction.

Thus, the mixed dialkyldithiophosphoric acid is prepared by the addition to phosphorus pentasulfide of four equivalents (or a slight excess thereof) of a mixture of a lower alcohol and a higher alcohol. The zinc dialkyldithiophosphate is then formed by the addition of 1.0 to 1.5 equivalents of a basically reacting zinc compound along with the ammonium salt, optionally in the presence of a polar promoter such as water, acetic acid, nitric acid, ammonium acetate and the like.

Preferably, the pH of the resulting mixed zinc dialkyldithiophosphate should be maintained between 5.5 and 7.0 and most preferably between 6.0 and 6.5. Normally, the pH of the resulting zinc composition is controlled by controlling the amount of excess of the basically reacting zinc compound employed.

The resulting mixed zinc dialkyldithiophosphate compositions of this invention are useful as anti-oxidant and anti-corrosion additives in lubricating oils. The lubricating oil used with the additive compositions of this invention may be mineral oil or synthetic oils of lubricating viscosity and preferably suitable for use in the crankcase of an internal combustion engine. Crankcase lubricating oils ordinarily have a viscosity of about 1300 cst 0° F. to 22.7 cst at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_{6-12}$ alpha olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Additive concentrates are also included within the scope of this invention. They usually include from about 90 to 10 weight percent of an oil of lubricating viscosity and from about 10 to 90 weight percent of the complex additive of this invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although an oil of lubricating viscosity may be used.

Other additives which may be present in the formulation include rust inhibitors, foam inhibitors, corrosion inhibitors, metal deactivators, pour point depressants, antioxidants, and a varity of other well-known additives.

Additionally, we have found that when ammonium acetate is employed as the ammonium salt in this invention it is compatible with crankcase lubricating oil used in either a diesel or gasoline engine. That is to say that the addition of the ammonium acetate to the mixed zinc does not produce an adverse effect on the engine such as excessive wear or the like.

The following examples are offered to specifically illustrate the invention. These examples and illustrations are not be be construed in any way as limiting the scope of the invention.

EXAMPLES

Example 1

Preparation of Zinc Isopropyl-2-Ethylhexel Dithiophosphate

Prepare a 70/30 mole ratio mixture of isopropanol to 2-ethylhexanol by mixing 544 gm of isopropanol and 506 gm of 2-ethylhexanol. Add 350 gm of this mixture to a three liter three neck round bottom flask equipped with a mechanical stirrer and with a venting system to a 25 percent sodium hydroxide scrubber. Add phosphorus pentasulfide (732 gm) to the system in portions over a period of time. Since this addition is exothermic, maintain the system during addition at approximately 71° C. by an external ice-water bath. To the stirred slurry, add an additional 700 gm of the isopropanol/2-ethylhexanol mixture to the system over approximately 2 hours while maintaining the temperature of the system at 71° C. Stir the system for an additional 5 hours at 71° C. and then cool to approximately 54° C. Suction filter the product through paper and then sparge it with nitrogen to give the isopropyl-2-ethylhexyldithiophosphoric acid having a total acid number (TAN) of 205.

Add isopropyl-2-ethylhexyldithiophosphoric acid (91.2 gm) and ammonium acetate (2.33 gm) to a three neck round bottom flask equipped with a mechanical stirrer. Add 46.6 gm of zinc oxide (1.15 equivalents based upon the TAN of the total dithiophosphoric acid employed) to the system. Hold the temperature at approximately 71° C. and add an additional 182.8 gm of the isopropyl-2-ethylhexyldithiophosphoric acid to the system. Maintain the temperature of 71° C. for an additional 5 hours. Strip the water from the system under reduced pressure at 71° C. for 30 minutes. Add celite and filter to give the titled product containing an effective amount of ammonium acetate to prevent precipitation or crystallization of the titled product.

Example 2

Alternate Preparation of Zinc Isopropyl-2-Ethylhexyl Dithiophosphate

Add isopropyl-2-ethylhexyldithiophosphoric acid (274 gm with a TAN of 205) and 2.33 gm of ammonium acetate to a three neck round bottom flask equipped with a mechanical stirrer. Add 46.6 gm of zinc oxide (1.15 equivalents based upon the TAN of the total dithiophosphoric acid employed) to the system. Hold the temperature at approximately 71° C. for 3 hours. Strip the water from the system under reduced pressure at 71° C. for 30 minutes. Add celite and filter to give the title compound containing an effective amount of ammonium acetate to prevent precipitation or crystallization of the titled product.

What is claimed is:

1. In a process for the preparation of a mixed zinc dialkyldithiophosphate by the reaction of phosphorus pentasulfide with from about 50–80 mole percent of lower alcohol and from about 50–20 mole percent of higher alcohol followed by neutralization of the resulting mixed dialkyldithiophosphoric acid with a basically reacting zinc compound, wherein the improvement comprises the addition to said reaction of an effective amount of an ammonium salt of a carboxylic acid having from 1 to 6 carbon atoms to prevent precipitation of said mixed zinc composition.

2. The method of claim 1 wherein the said lower alcohol is isopropanol and the said higher alcohol is 2-ethylhexanol.

3. The method of claim 2 wherein the said mixed zinc dialkyldithiophosphate is prepared from a mixture comprising about 70 mole percent isopropanol and about 30 mole percent 2-ethylhexanol.

4. The method of claim 1 wherein the carboxylic acid is acetic acid.

5. The method of claim 1 wherein 0.5 to 2.0 percent by weight of an ammonium salt of a carboxylic acid having from 1 to 6 carbon atoms is added to said reaction.

* * * * *